United States Patent [19]

Griffith et al.

[11] Patent Number: 5,362,639

[45] Date of Patent: Nov. 8, 1994

[54] METHOD TO INCREASE ANAEROBIC FERMENTATION RATES

[75] Inventors: Edward J. Griffith, Manchester; Toan M. Ngo, Eureka, both of Mo.

[73] Assignee: Monsanto Company, St. Louis, Mo.

[21] Appl. No.: 43,227

[22] Filed: Apr. 6, 1993

Related U.S. Application Data

[62] Division of Ser. No. 639,452, Jan. 10, 1991, abandoned.

[51] Int. Cl.$^5$ .................. C12P 7/06; C12N 1/16; C12N 1/18
[52] U.S. Cl. .................. 435/161; 435/255.1; 435/255.7; 435/801
[58] Field of Search ............... 435/157, 244, 255, 256, 435/801, 942, 161, 255.1, 255.7

[56] References Cited

U.S. PATENT DOCUMENTS

| 4,529,701 | 7/1985 | Seely | 435/244 |
|---|---|---|---|
| 4,727,031 | 2/1988 | Brown et al. | 435/244 |
| 4,808,526 | 2/1989 | Lawford | 435/244 |
| 4,808,527 | 2/1989 | Lawford | 435/813 |
| 4,812,410 | 3/1989 | Lawford | 435/244 |
| 4,816,399 | 3/1989 | Lawford | 435/244 |
| 4,840,902 | 6/1989 | Lawford | 435/244 |
| 4,845,033 | 7/1989 | Tegtmeier | 435/162 |
| 4,910,144 | 3/1990 | Saito et al. | 435/256 |

FOREIGN PATENT DOCUMENTS 8302952  9/1983  WIPO .

OTHER PUBLICATIONS

Jones et al, Process Biochemistry, Apr./May 1981, pp. 42–49.

*Primary Examiner*—Douglas W. Robinson
*Assistant Examiner*—Susan M. Dadio
*Attorney, Agent, or Firm*—R. C. Loyer

[57] ABSTRACT

There is disclosed a process for the fermentation by yeast of sugar to alcohol wherein a portion of the nutrient phosphate is provided by one or more condensed phosphates. It has been found that when condensed phosphates are employed as the nutrient source the fermentation rate increases. In addition, the rate increase is only observed when an increase in macronutrient elements is provided in conjunction with the condensed phosphates to compensate for the elements sequestered by the condensed phosphates.

8 Claims, No Drawings

METHOD TO INCREASE ANAEROBIC FERMENTATION RATES

This is a division of application Ser. No. 07/639,452, filed Jan. 10, 1991, now abandoned.

FIELD OF THE INVENTION

The present invention relates to a nutrient composition suitable for increasing the alcohol fermentation rate, and a method of using the composition. More specifically, the present invention relates to a nutrient composition comprising a nitrogen source and a combination of orthophosphate and phosphate polymers to increase the alcohol fermentation rate.

BACKGROUND OF THE INVENTION

Since 1972, the increases of the real cost of oil has prompted the evaluation of alternative technologies for the production of liquid fuels. Of particular interest is the use of biomass derived alcohol as a gasoline substitute or supplement. In view of this increased interest, the present invention provides a nutrient composition that is suitable for increasing the fermentation rate by yeast to provide alcohol.

Glucose is converted to ethanol by yeast fermentation according to the following equation:

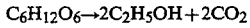

$$C_6H_{12}O_6 \rightarrow 2C_2H_5OH + 2CO_2$$

Additionally, quantities of glycerol and higher alcohols are also produced, the amount being dependent on the strain of yeast and fermentation conditions. Such reactions are catalyzed by enzymes.

Nitrogen and phosphorus are two of the essential elements for the growth of yeast. It is often necessary to supplement nitrogen and phosphorus sources, and occasionally other nutrients and micronutrient, to increase the acohol fermentation rate. Typically, supplemental phosphorus is provided as the orthophosphate.

U.S. Pat. No. 4,727,031, disclosed studies of aerobic systems using bacteria, that indicated, generally, the growth rate of bacteria decreased as the phosphate chain length increased. A synergistic combination of orthophosphate and a short chain condensed phosphate such as pyrophosphate or tripolyphosphate in a nutrient system was used to stimulate growth of aerobic bacteria. The nutrient system was such that 5% to 65% by weight of the total phosphate combination was the pyrophosphate and/or tripolyphosphate.

International Patent Publication No. WO 83/02952 disclosed the use of the inorganic pyrophosphate ions to stimulate the growth of some anaerobic or aerobic bacteria. The pyrophosphate ion oxidizes adenosine diphosphate (ADP) to adenosine tripolyphoshate (ATP) in anaerobic bacteria. ATP is known to be the primary carrier of chemical energy in biological processes, and therefore, stimulates the growth of the bacteria.

The above publications fail to disclose the use of polyphosphate, such as tripolyphosphate and Kurrol's salt, in combination with orthophosphate salts, or certain nutrients in combination with phosphate polymers to increase the fermentation rates of yeasts.

SUMMARY OF THE INVENTION

The present invention comprises a process for increasing the fermentation rate of yeast in the conversion of sugars to alcohol and an improved nutrient broth having an effective amount of a nutrient for the fermentation environment. The nutrient broth comprising typically a nitrogen source, a mineral base which includes microelements, macroelements and a phosphate source is provided with a condensed phosphate having more than one —P—O—P— linkage as at least a portion of the energy source for the yeast. Also, in accordance with this invention increased amounts of the macroelements magnesium and calcium are added to compensate for the loss of availability of such metals to the yeast due to sequestration by the condensed phosphate. It has been discovered that increased amounts of macroelements such as calcium and magnesium are required for increased rates of production of alcohol from the fermentation process when condensed phosphates are employed as at least a portion of the energy source form the yeast.

DETAILED DESCRIPTION OF THE INVENTION

Fermentation technology is well known and well documented. R. P. Jones, N. Pamment, and P. F. Greenfield, *Process Boichem*, 16(3), 42(1981), which is hereby incorporated by reference, discloses the effects of the environment and other variables on fermentation rates of yeasts for ethanol production from saccharine materials, such as sugars.

The micro-organisms most suitable for the production of ethanol from sugars are yeasts of the genera Saccharomyces and Kluyveromyces. A preferred yeast is *S. cerevisiae*, because of its ability to tolerate adverse environmental conditions.

The substrate for the fermentation can be prepared from one or more sugars. The sugars can be refined sugars or can be derived from raw materials such as agricultural or processing wastes or crops grown for the purpose of fermentation. Examples of such sugars includes glucose, maltose, maltotriose, galactose, mannose, fructose, sucrose, raffinose and deoxyribose. Examples of suitable raw materials includes cane sugar, beet sugar, molasses, cannery wastes, corn, sweet sorghum, other grains, cassava, potatoes, jerusalem artichokes, sago, taro, wood, wood wastes, agricultural residues, municipal wastes and whey.

The condensed phosphates of the present invention having more than one —P—O—P— linkage include known polymers, for example, of the formula $[K(PO_3)]_n$, where n is from about 3 to 10,000, potassium tripolyphosphate (KTP), potassium metaphosphate, sodium hexametaphosphate. When n of the above formula is about 1,000 or more, the polymer is called potassium Kurrol's salt, also known as potassium metaphosphate. Salts other than the potassium salt can be used, such as sodium salts, but in that case, another source of potassium must be provided.

The combination of orthophosphate and pyrophosphate (the dimer) is generally ineffective in the present invention, resulting in a lower fermentation rate than the orthophosphate alone. KTP is more effective, on an equal weight basis, in increasing fermentation rates, and is therefore a preferred nutrient. The amount of condensed phosphate in the total phosphate nutrient can vary widely, in the range of about 5 to 75 weight %. A preferred range is from about 40 to about 60 weight %.

Increasing the glucose concentration in the nutrient increases the ethanol yield and the fermentation rate. However, at higher glucose concentrations, precipitation of the nutrients and the resulting unavailability of the nutrients to the yeast may be a problem.

As is known in the art, additional nutrients must be provided to the nutrient system, such as nitrogen and sulfur, typically in the form of $(NH_4)_2SO_4$. The yeast also requires macroelements such as magnesium, calcium, zinc, iron, manganese and chlorine.

It has been discovered that when using the condensed phosphate of the present invention, it is necessary to increase the amounts of macroelements such as magnesium and calcium if an increase in the rate of alcohol production is to be expected. It is believed that the reason for the required increase in the amount of such metals is that the phosphate polymers sequester metals such as calcium and magnesium, and therefore such sequestered metals become less readily available as nutrients for the yeast.

In accordance with this invention the nutrient systems are provided with sufficient additional macroelements, particularly such as calcium and magnesium so as to provide an adequate mineral base available to the yeast in the nutrient system required for fermentation to proceed at the increased rate provided by the process of this invention. If too much calcium or magnesium is added, the condensed phosphate can precipitate and this, of course, will render the the precipitate unavailable to the fermentation process.

Typically the amount of magnesium added to the nutrient system over and above the usual mineral base is in the range of from about 0.0368 mg to about 0.0789 mg/ml of nutrient solution. The amount of calcium added to the nutrient system over and above the mineral base usually added is in the range of from about 0.1541 mg to about 0.4137 mg/ml of nutrient solution. If an increase of said macroelements in the above mentioned ranges are not provided when employing the condensed phosphates of this invention in the nutrient solutions, it has been found that the rate of alcohol production actually decreases when condensed phosphates of this invention are employed as the energy supply in lieu of Adenosine triphosphate.

Additional elements, called microelements, are are part of the mineral base and known in the art to be required for fermentation. Such microelements include, for example, cobalt, boron, cadmium, chromium, copper, iodine, molybdenum, nickel and vanadium and are also included in the nutrient system and process of this invention.

Experimental

Fermentation procedures are well known in the art. C. H. Chang and J. Hong, *Biotechnol. Bioeng.*, 26, 797 (1984), which is hereby incorporated by reference, discloses a laboratory procedure which is similar to that used in the present invention.

In the following examples, phosphate polymers are partially substituted for orthophosphate, to determine the effect of substituting a combination of polyphosphate and orthophosphate for orthophosphate alone. Sodium hexametaphosphate (SHMP) was used to solubilize the potassium Kurrol's salt ($[K(PO_3)]_n$, where $K_2O/P_2O_5$ equals 0.98). Without the SHMP, the Kurrol's salt tends to be insoluble and is unavailable as nutrient to the yeast. Amounts of magnesium and calcium are added to maintain the mineral base by compensating for the metals sequestered by the condensed phosphates.

PREPARATION OF PURE CULTURE

A vial of pure culture of freeze dried *Saccharomyces cerevisae* (s.c.) code 41026 obtained from ATCC was placed in a 1.0 l flask containing 200 ml Diffco brand Y.M. broth (nutrient solution for s.c.) containing 14% by weight glucose. The solution was incubated aerobically at 26° C. with shaking at 200 hz for about 12 h. The solution was diluted with glycerol to form a 10% glycerol solution with an optical density of 2.7 at 550 nm. Aliquots of 10.0 ml of the solution were transferred into sterile 15 ml plastic, disposable, sterile centrifuge tubes for storage at $-70°$ C. for later use.

PREPARATION OF STERILIZED SOLUTIONS

Into a 4 oz. glass bottle was placed 8 g Fisher reagent grade $MgSO_4 \cdot 7H_2O$. The volume was brought to 50 g with distilled water to provide a concentration of 0.16 g of magnesium sulfate per g of solution. The solution was sterilized at 121° C. for 0.5 h at 15 psig. The solution was cooled before using.

A calcium chloride solution was prepared utilizing the same procedure as was used for the Mg solution, except that the $CaCl_2$ solution was filtered to remove insoluble impurities. The calcium chloride solution contained 0.16 g of calcium chloride per g of solution.

PREPARATION OF GLUCOSE SOLUTION

Into a 2 l flask was placed 225 g of Difco brand glucose and diluted to 1500.0 g with distilled water. The mixture was stirred. The top of the flask was covered with aluminum foil, and the solution sterilized for 0.5 h at 121° C. and 15 psig. The 15 weight % solution was cooled before using.

Preparation of Nutrient Medium

Solution A

Into a 10 oz glass bottle were placed 1.2 g $KH_2PO_4$, 1.4 g $K_2HPO_4$, 0.4 g $MgSO_4 \cdot 7H_2O$, 30.0 g $NH_4SO_4$ (all Fisher reagent grade) and 1.6 g Difco brand yeast extract. The sample was brought to 100 g with distilled water and stirred until the solids dissolved. The bottle was loosely capped and sterilized at 121° C. for 0.5 h and 15 psig.

Solution B

Solution B was prepared in the same manner as Solution A, except that 1.4 g $K_2HPO_4$ was omitted.

Solution C

Solution C was prepared the same manner as Solution A except that it contained 2.85 g $KH_2PO_4$, 0.8 g $MgSO_4 \cdot 7H_2O$, 59.0 g $NH_4SO_4$ and 3.2 g yeast extract which were diluted to 200 g with distilled water.

Solution D

Solution D was prepared the same as Solution A, except that 1.56 g $KH_2PO_4$ was used and the $K_2HPO_4$ was omitted.

PREPARATION OF STERILIZED CONDENSED PHOSPHATES

The following solid condensed phosphate samples were sterilized dryly in a beaker at 125° C. for 3 h: potassium tripolyphosphate $k_5P_3O_{10}$ (KTP), tetrapotassium pyrophosphate $K_4P_2O_7$ (TKPP), sodium hexametaphosphate (SHMP) and potassium Kurrol's salt (KKS) ($[K(PO_3)]_n$, where n is about 1000 and the ratio $K_2O/P_2O_5$ is 0.98). Potassium carbonate, $K_2CO_3$ was also sterilized in this manner.

FERMENTATION EXPERIMENTS

In the following experiments (Control 1 and modified control 2, and Examples 3 through 10, shown in Table 1) the nutrient systems contained 15 weight % glucose. The additional amounts of calcium and magnesium were added as shown in Table 1 to overcome the lose of these metals to the system by sequestration resulting from the addition of the condensed phosphates. Potassium Kurrol's salt plus sodium hexametaphosphate was used in combination with orthophosphate (monopotassium orthophosphate $KH_2PO_4$).

EXPERIMENTAL PROCEDURE

Into a 250 ml flask were placed 125 ml of 15% by weight glucose solution, 25 ml nutrient medium of 15% concentration or 30 ml if 20% concentration, 0.9 ml calcium solution and 0.60 ml magnesium solution. The pH of the solution was adjusted with sulfuric acid to the range of about 4.3 to 5.0. To the solution was added 400 microliter of pure s.c. culture (prepared above). The solution was fermented anaerobically at 30° C. +/−2 degrees for the indicated elapsed times. During the course of the fermentation, the pH of the solution dropped below 4.0 and was adjusted with NaOH solution to between 4.3 and 5.0.

The rates of ethanol formation per unit of time as shown in Tables 3 and 6 below were determined by measuring the amount of alcohol produced at specified times as determined by proton NMR analysis. The following equations were used for the determination of alcohol formation on a weight percent basis at any given time during the course of fermentation.

$$\frac{A_k}{C_k} = \frac{A_{unk}}{C_{unk}}$$

$$C_{unk} = \frac{A_{unk}}{A_k} \times C_k$$

wherein $A_k$ and $A_{unk}$, respectively, are areas of known and experimental solutions, obtained from the NMR. $C_k$ and $C_{unk}$, respectively, are the ethanol concentrations in weight percent of the control and experimental solutions.

The concentrations of ethanol in the solutions, in weight percent, at any given time during the course of fermentation are converted to grams of ethanol per 100 grams of solution (g EtOH/100 g sol.) by the following manipulation:

100−% w/w EtOH=N g EtOH/100 g sol.=%w/w EtOH×100/N

In Table 1 below the test solutions are summarized wherein Run 1 is a control and Run 2 is a control modified by the incorporation of additional calcium and magnesium solutions prepared as noted above. In Runs 3–7, sodium hexametaphosphate was added in addition to the phosphate polymer for the purpose of solubilizing potassium Kurrol's salt.

TABLE 1

| Run | Ca ml. sol. | Mg ml. sol. | NUTRIENT | Total Phosphates as mol P | Condensed Phosphate as mol P |
|---|---|---|---|---|---|
| 1. | 0 | 0 | A | 0.0168 | |
| 2. | 0.98 | 0.60 | A | 0.0168 | |
| 3.* | 0.81 | 0.53 | B | 0.0124 | .0011 KKS+ .0025 SHMP |
| 4.* | 0.89 | 0.53 | C | 0.0147 | .0013 KKS+ .0029 SHMP |
| 5.* | 0.90 | 0.60 | C | 0.0147 | .0013 KKS+ .0029 SHMP |
| 6.* | 0.81 | 0.53 | D | 0.0161 | .0014 KKS+ .0032 SHMP |
| 7.* | 0.90 | 0.60 | D | 0.0161 | .0014 KKS+ .0032 SHMP |
| 8. | 0.90 | 0.60 | C | 0.0131 | .0026 TKPP |
| 9. | 0.90 | 0.60 | C | 0.0135 | .003 KTP |
| 10. | 0.90 | 0.53 | C | 0.0135 | .003 KTP |

*.05 g $K_2CO_3$ added

The above described solutions were employed in the fermentation process for the conversion of glucose to alcohol. The results in Table 2 are shown in percent of ethanol concentration in the fermentation medium and also in actual weight in grams (g).

TABLE 2

Weight % Ethanol Concentration in Medium Versus Time (15% Glucose Solution)

| Run | Time 15:10 % | g | Time 18:35 % | g | Time 22:35 % | g | Time 26.45 % | g | Time 29.55 % | g | Time 37.30 % | g |
|---|---|---|---|---|---|---|---|---|---|---|---|---|
| 1 | 0.2762 | 0.28 | 0.7570 | 0.76 | 1.6572 | 1.69 | 2.6801 | 2.75 | 3.4169 | 3.54 | 4.2760 | 4.47 |
| 2 | 0.2864 | 0.29 | 0.8286 | 0.84 | 1.6777 | 1.71 | 2.7006 | 2.77 | 3.3348 | 3.45 | 4.2760 | 4.47 |
| 3 | 0.3273 | 0.33 | 0.9514 | 0.96 | 1.8618 | 1.90 | 2.8029 | 2.88 | 3.5804 | 3.71 | 4.4806 | 4.69 |
| 4 | 0.2967 | 0.30 | 0.9513 | 0.96 | 1.8209 | 1.85 | 2.8234 | 2.91 | 3.5394 | 3.67 | 4.4601 | 4.67 |
| 5 | 0.3478 | 0.35 | 0.9411 | 0.95 | 1.8618 | 1.90 | 1.9461 | 3.04 | 3.6622 | 3.80 | 4.5420 | 4.76 |
| 6 | 0.3990 | 0.40 | 0.9411 | 0.95 | 1.8004 | 1.83 | 2.7313 | 2.81 | 3.2939 | 3.41 | 4.5420 | 4.76 |
| 7 | 0.4194 | 0.42 | 0.9616 | 0.97 | 1.8925 | 1.93 | 2.8847 | 2.97 | 3.6213 | 3.76 | 4.3373 | 4.53 |
| 8 | 0.2762 | 0.28 | 0.8081 | 0.81 | 1.7799 | 1.81 | 2.5983 | 2.67 | 3.5394 | 3.67 | 4.4908 | 4.70 |
| 9 | 0.4296 | 0.43 | 0.9820 | 0.99 | 2.0459 | 2.09 | 2.9666 | 3.06 | 3.5804 | 3.71 | 4.5215 | 4.74 |
| 10 | 0.4194 | 0.42 | 0.9922 | 1.00 | 1.9027 | 1.94 | 3.0484 | 3.14 | 3.7747 | 3.92 | 4.4601 | 4.67 |

The percent change in rate of ethanol formation, as shown in Table 3, was determined according to the following formula:

$$\frac{[(C_1 - C_2)] \times 100}{C_2} = \% \text{ change}$$

where C is the concentration of ethanol under the given time and conditions. $C_1$ is the concentration of the test sample while $C_2$ is the concentration of the control. Two comparisons are shown is Table 3. First, Run 1, control, is compared to modified control, Run 2 and test Runs 3–10 employing the process of this invention. Then, Run 2 is compared to Run 1, control, and test Runs 3–10. In Table 3 the term Rate indicates alcohol production in grams of ethanol per hour and the percent change in rate is indicated as calculated above. As can be seen from the data in Table 3 below, improvement of over 15% with respect to change in rate is shown by the process of this invention.

TABLE 3

| | Run 1, Control | | Run 2, Control | |
|---|---|---|---|---|
| Run | Rate | % Change | Rate | % Change |
| 1. | 0.2283 | N/A | 0.2283 | 0.70 |
| 2. | 0.2267 | −0.7008 | 0.2267 | N/A |
| 3. | 0.2483 | 8.76 | 0.2483 | 9.53 |
| 4. | 0.2433 | 6.57 | 0.2433 | 7.32 |
| 5. | 0.2567 | 12.44 | 0.2567 | 13.23 |
| 6. | 0.2333 | 2.19 | 0.2333 | 2.91 |
| 7. | 0.2500 | 9.51 | 0.2500 | 10.28 |
| 8. | 0.235 | 2.93 | 0.235 | 3.66 |
| 9. | 0.2550 | 11.70 | 0.2550 | 12.48 |
| 10. | 0.2617 | 14.63 | 0.2617 | 15.44 |

The experimental procedure employed to provide the data in Table 2 was repeated with the exception that the glucose solution employed was at 20% concentration instead of 15% concentration. The

TABLE 4

| Run | Ca ml. sol. | Mg ml. sol. | NUTRIENT | Total Phosphates as mol P | Condensed Phosphate as mol P |
|---|---|---|---|---|---|
| 11. | 0.94 | 0.63 | A | 0.0168 | |
| 12. | 0.94 | 0.63 | B | 0.0131 | .0013 KKS + .003 SHMP* |
| 13. | 0.94 | 0.63 | C | 0.0156 | .0016 KKS + .0035 SHMP* |
| 14. | 0.89 | 0.58 | C | 0.0156 | .0017 KKS + .0035 SHMP* |
| 15. | 0.89 | 0.58 | D | 0.0170 | .0017 KKS + .0038 SHMP* |
| 16. | 0.94 | 0.63 | C | 0.0121 | .0033 KTP |
| 17. | 1.0 | 0.65 | C | 0.0121 | .0033 KTP |

*.05 g $K_2CO_3$ added

The amounts of ethanol formation versus time for the above described nutrient systems 11–17 are shown in Table 5 below as determined by proton NMR analysis of the amount of ethanol in solution at various specified times. As in Table 2 above, the data in Table 5 shows the amounts of ethanol in both percent concentration in the nutrient system as well as in grams.

TABLE 5

| | Weight % Ethanol Concentration in Medium Versus Time | | | | | | | | | | | | | |
|---|---|---|---|---|---|---|---|---|---|---|---|---|---|---|
| | Time 17:10 | | Time 10:40 | | Time 22:20 | | Time 26:45 | | Time 28:45 | | Time 38:15 | | Time 41:50 | |
| Run | % | g | % | g | % | g | % | g | % | g | % | g | % | g |
| 1 | 0.6152 | 0.62 | 1.2531 | 1.27 | 2.0050 | 2.05 | 3.1442 | 3.25 | 3.5315 | 3.66 | 5.6732 | 6.01 | 6.3795 | 6.81 |
| 2 | 0.7519 | 0.76 | 1.2759 | 1.29 | 2.0050 | 2.05 | 3.3036 | 3.42 | 3.6910 | 3.83 | 5.4682 | 5.78 | 6.2656 | 6.68 |
| 3 | 0.7974 | 0.80 | 1.3898 | 1.41 | 2.1644 | 2.21 | 3.4860 | 3.61 | 4.0100 | 4.18 | 5.9694 | 6.35 | 6.3909 | 6.83 |
| 4 | 0.7861 | 0.79 | 1.2987 | 1.32 | 2.0734 | 2.12 | 3.2809 | 3.39 | 3.6910 | 3.83 | 5.8327 | 6.19 | 6.2542 | 6.67 |
| 5 | 0.8430 | 0.85 | 1.4468 | 1.47 | 2.2101 | 2.26 | 3.5088 | 3.64 | 4.1239 | 4.30 | 6.2656 | 6.68 | 6.8808 | 7.39 |
| 6 | 0.8886 | 0.90 | 1.5038 | 1.53 | 2.2556 | 2.31 | 3.3948 | 3.51 | 4.0100 | 4.18 | 6.0606 | 6.45 | 6.4023 | 6.84 |
| 7 | 0.9000 | 0.91 | 1.5038 | 1.53 | 2.2784 | 2.33 | 3.5543 | 3.69 | 4.0100 | 4.18 | 6.4251 | 6.87 | 6.8580 | 7.36 |

The change in rates of ethanol formation for nutrient solutions 11–17 above, are shown in Table 6 below for the runs employing the 20% concentration of glucose. The rates were determined by the formula given above. The rate expressed in Table 6 is in grams of ethanol per hour produced by the nutrient broth as indicated by the amount of alcohol present. The percent change in rate is compared to Run 11 which is a control.

TABLE 6

| Run | Rate | Percent Change |
|---|---|---|
| 11. | .2567 | NA |
| 12. | .2700 | 5.18 |
| 13. | .2717 | 5.84 |
| 14. | .2733 | 6.47 |
| 15. | .3000 | 16.87 |
| 16. | .2883 | 12.31 |
| 17. | .2867 | 11.69 |

The above data indicates that the rate of alcohol production is increased as much as over 16% by the addition of the condensed phosphate and increased amounts of the macroelements of magnesium and calcium.

We claim:

1. In a process for the conversion of sugars to alcohol by yeast fermentation in a nutrient broth under anaerobic conditions, wherein the nutrient broth comprises a nitrogen source and a mineral base, said mineral base comprises microelements, macroelements and a phosphorus source, and wherein said phosphorous source comprises at least one condensed phosphate, the improvement comprising adding to said nutrient broth calcium and magnesium, in amounts sufficient to overcome the loss of said calcium and said magnesium due to sequestration resulting from the presence of condensed phosphate or phosphates, so as to maintain calcium and magnesium levels in the nutrient broth for assimilation by the yeast and whereby the rate of conversion of sugars to alcohol is increased.

2. The process of claim 1 wherein the condensed phosphate is selected from the group consisting of potassium tripolyphosphate, potassium trimetaphosphate, potassium Kurrol's salt or combinations thereof.

3. The process of claim 2 wherein the condensed phosphate comprises from about 5 to 75 weight % of the total phosphate source.

4. The process of claim 3 wherein the condensed phosphate comprises from about 40 to about 60 weight % of the total phosphate source.

5. The process of claim 1 wherein the amount of calcium added to the nutrient solution is in the range of from about 0.1541 mg/ml to 0.4237 mg/ml of nutrient solution.

6. The process of claim 1 wherein the amount of magnesiums added to the nutrient broth is in the range of from about 0.0368 mg/ml to 0.0789 mg/ml of nutrient solution.

7. The process of claim 2 wherein the phosphate is Kurrol's salt.

8. The process of claim 7 further comprising a solubilizing amount of phosphate salt to solubilize the Kurrol's salt.

* * * * *